(12) United States Patent
Nebolsin et al.

(10) Patent No.: US 11,584,709 B2
(45) Date of Patent: Feb. 21, 2023

(54) MULTITARGET DRUG FOR TREATING DISEASES IN MAMMALS

(71) Applicant: "PHARMENTERPRISES EURASIA" LIMITED LIABILITY COMPANY, Moscow (RU)

(72) Inventors: Vladimir Evgenievich Nebolsin, Der. Borzye (RU); Tatyana Alexandrovna Kromova, Khimki (RU); Anastasia Vladimirovna Rydlovskaya, St. Petersburg (RU)

(73) Assignee: "PHARMENTERPRISES EURASIA" LIMITED LIABILITY COMPANY, Moscow (RU)

( * ) Notice: Subject to any disclaimer, the term of this patent is extended or adjusted under 35 U.S.C. 154(b) by 237 days.

(21) Appl. No.: 16/472,171

(22) PCT Filed: May 24, 2018

(86) PCT No.: PCT/RU2018/050057
§ 371 (c)(1),
(2) Date: Jun. 20, 2019

(87) PCT Pub. No.: WO2018/217138
PCT Pub. Date: Nov. 29, 2018

(65) Prior Publication Data
US 2021/0284600 A1     Sep. 16, 2021

(30) Foreign Application Priority Data
May 26, 2017   (RU) ............... RU2017118351

(51) Int. Cl.
| A61K 31/215 | (2006.01) |
| C07C 235/34 | (2006.01) |
| A61P 1/12 | (2006.01) |
| A61K 9/00 | (2006.01) |
| A61K 45/06 | (2006.01) |

(52) U.S. Cl.
CPC .......... C07C 235/34 (2013.01); A61K 9/0053 (2013.01); A61K 45/06 (2013.01); A61P 1/12 (2018.01)

(58) Field of Classification Search
CPC .................................................. A61K 31/215
See application file for complete search history.

(56) References Cited

U.S. PATENT DOCUMENTS 8,309,766 B2 * 11/2012 Nebolsin ............... C07C 233/51
560/41

FOREIGN PATENT DOCUMENTS

| EA | 201201167 A1 | 4/2013 |
| WO | WO-2006101422 A1 | 9/2006 |

OTHER PUBLICATIONS

International Search Report and Preliminary Report on Patentability for International Application No. PCT/RU2018/050057 dated Sep. 20, 2018, 15 pages. (9 pages Original Copy, 6 pages English translation).

* cited by examiner

*Primary Examiner* — Rei Tsang Shiao
(74) *Attorney, Agent, or Firm* — BCF LLP

(57) ABSTRACT

The invention relates to the chemistry of organic compounds, pharmacology and medicine and concerns therapy for obesity, psoriasis, Crohn's disease, colitis, irritable bowel syndrome, diarrhea, nausea and vomiting, as well as a number of other diseases associated with the activity of cathepsin S, cannabinoid receptors type 1, tachykinin receptors type 1 and 2, prokineticin receptors type 1 and 2, bradykinin receptors type 1, melanocortin receptors MC4R, serotonin receptors 5-HT2B and NB-kB signaling pathway, by using benzyl (2S)-2-[2-(4-hydroxyphenyl)acetamido]-3-phenylpropanoate compound.

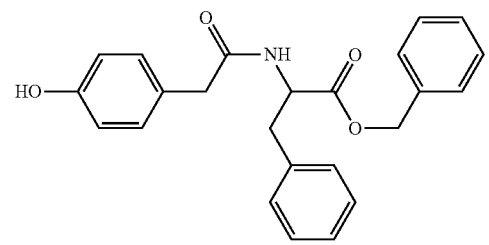

The compound and pharmaceutically acceptable adducts, hydrates and solvates thereof are a cathepsin S inhibitor, cannabinoid receptor type 1 agonist, tachykinin receptor type 1 and 2 antagonist, prokineticin receptor type 1 and 2 antagonist, bradykinin receptor type 1 antagonist, melanocortin receptor MC4R antagonist, serotonin receptor 5-HT2B antagonist, and NB-kB signaling pathway inhibitor. The invention also relates to pharmaceutical compositions comprising a therapeutically effective amount of the compound according to the invention.

2 Claims, No Drawings

MULTITARGET DRUG FOR TREATING DISEASES IN MAMMALS

CROSS REFERENCE TO RELATED APPLICATIONS

This application is a national stage application under 35 U.S.C. § 371 of International Application No. PCT/RU2018/050057, filed internationally on May 24, 2018, which claims priority to Russian Application No. 2017118351, filed on May 26, 2017, the content of which is hereby incorporated by reference.

FIELD OF THE ART

The invention relates to the chemistry of organic compounds, pharmacology and medicine and concerns the therapy for obesity, psoriasis, Crohn's disease, colitis, irritable bowel syndrome, diarrhea, nausea and vomiting, as well as a number of other diseases by the use of a compound that is a cathepsin S inhibitor, cannabinoid receptor type 1 agonist, tachykinin receptor type 1 and 2 antagonist, prokineticin receptor type 1 and 2 antagonist, bradykinin receptor type 1 antagonist, melanocortin receptor MC4R antagonist, 5-HT2B serotonin receptor antagonist and NB-kB signaling pathway inhibitor.

PRIOR ART

Functional disorders of the gastrointestinal tract include a group of heterogeneous clinical conditions that are manifested by symptoms from the middle and lower parts of the gastrointestinal tract. Irritable bowel syndrome (IBS), colic, bloating, constipation and diarrhea are the most common disorders of the gastrointestinal tract. According to data of the World Gastroenterological Organization, the prevalence of IBS in Europe and North America is estimated at 10-15%. Worldwide, the disease affects about 11.2% of the population (Nat Rev Dis Primers, 2016, 2:16014). In the general structure of gastroenterological pathology, IBS ranks first in the United States, it accounts for 28% of all cases of consulting gastroenterologists. Another extremely common disorder of the gastrointestinal tract is diarrhea. The gold standard for treating diarrhea is currently loperamide, which is a mu-opioid receptor agonist of peripheral action. However, in some cases, including diarrhea, caused by taking chemotherapeutic drugs, the use of loperamide is ineffective. Infantile colic, manifested in infants from 6 weeks to 6 months, affects 10-30% of children, and is accompanied by an unreasonable strong cry that lasts more than 3 hours a day (Zhonghua Er Ke Za Zhi. 2017 Apr. 2; 55(4):314-317 The cause of this phenomenon is currently unknown, so an effective and safe way to relieve colic attacks has not yet been developed. In the 1980s, attempts were made to use cholinergic antagonists, but they were discontinued due to the high risk of side effects. The only drug approved for use in colic is simethicone, according to the results of a recently conducted meta-study, was ineffective. Thus, it can be argued that there is a need for the creation and introduction into the clinical practice of new effective drugs for the treatment of disorders of the gastrointestinal tract.

Tachykinin (neurokinin) receptors are a perspective group of therapeutic targets for innovative drugs for the treatment of diseases of the gastrointestinal tract. There are three types of tachykinin receptors: NK1, NK2 and NK3. These receptors are prevailing both in the central nervous system and in peripheral tissues. In the gastrointestinal tract (GIT) they are expressed in neurons and effector cells and affect intestinal motility, secretory and immune activities, visceral sensitivity and nociception (Holzer P. Tachykinins. In Handbook of Biologically Active Peptides (Second Edition); Kastin A. J., Ed.; Elsevier, 2013; pp. 1330-1337). In this regard, tachykinin receptors have proven to be potential targets for the treatment of functional GIT diseases, one of varieties of which is irritable bowel syndrome (IBS). The most studied and widely investigated receptors in connection with the treatment of functional bowel disease are the NK2 receptors (Br J Pharmacol, 2004, 141, 1249-63). The tachykinin NK2 receptors in the gastrointestinal tract are expressed in cells of the muscle layer, muscular layer of mucous tunic, enterocytes and immune cells, as well as in the excitatory and inhibitory neurons of the submucosa and muscle plexus (J Comp Neurol, 2007, 503, 381-91). The expression of NK2 receptors is increased in inflammatory cells of proper mucous plate and activated eosinophils around mucous crypts (Naunyn Schmiedebergs Arch Pharmacol, 2003, 367, 104-8). Therapeutic indications for NK1 and NK2 receptor antagonists include irritable bowel syndrome (Neurogastroenterol Motil. 2015 October; 27(10):1354-70, Br J Pharmacol. 2004 April; 141(8):1249-63), ulcerative colitis (Inflamm Res. 2014 May; 63(5):399-409), Crohn's disease (Neurogastroenterol Motil. 2011 May; 23(5):475-83, e179-80), diarrhea (Br J Pharmacol. 1997 June; 121(3):375-80), infantile colic (Neuropeptides. 2010 June; 44(3):269-72) postoperative ileus, nausea and vomiting (Am J Health Syst Pharm. 2017 Apr. 10), cough (Pulm Pharmacol Ther. 2004; 17(1): 11-8), asthma (Allergy. 2013 January; 68(1):48-54, BMC Pulm Med. 2011 Aug. 2; 11:41), rheumatoid arthritis (Neuropeptides. 1998 June; 32(3):215-23) and psoriasis (Pathobiology. 1999; 67(1):51-4).

Another possible treatment for gastrointestinal disorders is the use of CB1R cannabinoid receptor agonists. The CB1R receptor agonists slow down ion transport in the intestinal mucosa, reducing water accumulation. Probably, it is more than likely that the effect is mediated by interaction with nerve guides, rather than the direct effect on the intestinal epithelium. The ability of CB1 receptor agonists to weaken the intestinal motility, reduce the secretion and sensitivity of nerve endings can be used to treat patients with irritable bowel syndrome (J Pharmacol Exp Ther. 2014 July; 350(1):69-78) and diarrhea (Drug News Perspect. 2009 September; 22(7):383-92), including chemotherapy-induced diarrhea (Curr Gastroenterol Rep. 2015 February; 17(2): 429). Furthermore, CB1R cannabinoid receptor agonists can be used to treat neurodegenerative diseases (including Parkinson's disease, Alzheimer's disease, Huntington's disease (Handb Exp Pharmacol. 2015; 231:233-59), multiple sclerosis (J Med Chem. 2016 Jul. 28; 59(14):6753-71) and encephalomyelitis (Mult Scler Relat Disord. 2015 November; 4(6):505-11).

5-hydroxytryptamine receptor (5-HT3) antagonists are used to treat a pain associated with irritable bowel syndrome and other disorders of the gastrointestinal tract (Aliment Pharmacol Ther 1997; 11: 3-15). At the same time, antagonists of 5-hydroxytryptamine receptors 5-HT2B apparently can be useful not only to reduce the pain associated with the development of pathology, but also have a direct effect on the pathogenesis of the disease (Mini Rev Med Chem. 2004 March; 4(3):325-30). Furthermore, 5-hydroxytryptamine receptor 5-HT2B antagonists can be used to treat migraine (Expert Opin Investig Drugs. 2017 March; 26(3):269-277).

A relatively new and relatively insufficiently unexplored direction is the use of first and second type prokineticin receptor agonists for the treatment of disorders of the gastrointestinal tract and, in particular, irritable bowel syndrome (Neurogastroenterol Motil. 2012 January; 24(1):65-75). For the treatment of Crohn's disease, ulcerative colitis (Br J Pharmacol. 2013 January; 168(2):389-402) and a number of other diseases (ischemia (Stroke. 2009 January; 40(1):285-93), allergic asthma (Pharmacol Res. 2016 February; 104:132-9) and hyperglycemia (J Cardiovasc Pharmacol. 2012 July; 60(1):61-9)) it is possible to use BRDKB1 bradykinin receptor agonists. It should be noted that the functional response caused by the activation of a number of receptors is associated with the signal pathway of the transcription NF-kB factor. NF-kB signaling pathway inhibitors can be used to treat psoriasis (Int Immunopharmacol. 2015 February; 24(2):392-9), multiple sclerosis (J Neuroinflammation. 2015 Sep. 30; 12:184), ulcerative colitis (Mol Cell Biochem. 2016 August; 419(1-2):65-74), Crohn's disease (J Steroid Biochem Mol Biol. 2007 January; 103(1):51-60) and a number of other diseases.

Thus, today there are many therapeutic approaches to the treatment of disorders of the gastrointestinal tract. However, there is still no registered medicinal product acting on several of the recited mechanisms. Therefore, there remains a need for the creation and introduction into the clinical practice of new effective drugs for the treatment of disorders of the gastrointestinal tract and other diseases.

This invention relates to the use of benzyl (2S)-2-[2-(4-hydroxyphenyl)acetamido]-3-phenylpropanoate compound or its adduct, hydrate, solvate, which is a cathepsin S inhibitor, cannabinoid receptor type 1 agonist, tachykinin receptor type 1 and 2 antagonist, prokineticin receptor type 1 and 2 antagonist, bradykinin receptor type 1 antagonist, melanocortin receptor MC4R antagonist, 5-HT2B serotonin receptor antagonist and NB-kB signaling pathway inhibitor, in the treatment of obesity, psoriasis, Crohn's disease, colitis, irritable bowel syndrome, diarrhea, nausea and vomiting, as well as a number of other diseases.

DISCLOSURE OF THE INVENTION

It is an object of the present invention to develop a new drug that is a cathepsin S inhibitor, cannabinoid receptor type 1 agonist, tachykinin receptor type 1 and 2 antagonist, prokineticin receptor type 1 and 2 antagonist, bradykinin receptor type 1 antagonist, melanocortin receptor MC4R antagonist, 5-HT2B serotonin receptor antagonist and NB-kB signaling pathway inhibitor, and is effective in the treatment of obesity, psoriasis, Crohn's disease, colitis, irritable bowel syndrome, diarrhea, nausea and vomiting.

The technical result of the invention is the development and obtainment of the effective cathepsin S inhibitor, cannabinoid receptor type 1 agonist, tachykinin receptor type 1 and 2 antagonist, prokineticin receptor type 1 and 2 antagonist, bradykinin receptor type 1 antagonist, melanocortin receptor MC4R antagonist, 5-HT2B serotonin receptor antagonist and NB-kB signaling pathway inhibitor, characterized by high activity and pharmacokinetic characteristics allowing to use the compound in topical use, in the therapy of obesity, psoriasis, Crohn's disease, colitis, irritable bowel syndrome, diarrhea, nausea and vomiting, as well as other diseases associated with the activity of cathepsin S, cannabinoid receptors type 1, tachykinin receptors type 1 and 2, prokineticin receptors type 1 and 2, bradykinin receptors type 1, melanocortin receptors MC4R, serotonin receptors 5-HT2B and NB-kB signaling pathway.

The indicated technical result is achieved by the use of benzyl (2S)-2-[2-(4-hydroxyphenyl)acetamido]-3-phenylpropanoate compound (Compound 1)

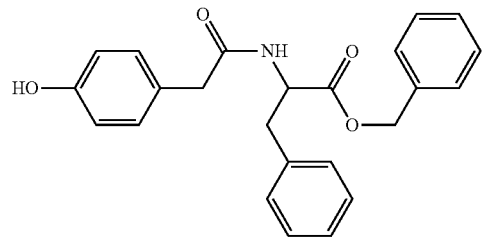 [SMILES: O=C(Cc1ccc(O)cc1)NC(Cc1ccccc1)C(=O)OCc1ccccc1]

or an adduct, hydrate solvate thereof as a cathepsin S inhibitor, cannabinoid receptor type 1 agonist, tachykinin receptor type 1 and 2 antagonist, prokineticin receptor type 1 and 2 antagonist, bradykinin receptor type 1 antagonist, melanocortin receptor MC4R antagonist, 5-HT2B serotonin receptor antagonist and NB-kB signaling pathway inhibitor.

Benzyl (2S)-2-[2-(4-hydroxyphenyl)acetamido]-3-phenylpropanoate compound is disclosed and described in international application WO 2006101422.

The present invention also relates to the use of benzyl (2S)-2-[2-(4-hydroxyphenyl)acetamido]-3-phenylpropanoate compound or an adduct hydrate, solvate thereof to produce a pharmaceutical composition for preventing and/or treating obesity, psoriasis, Crohn's disease, colitis, irritable bowel syndrome, diarrhea, nausea and vomiting, and also other disorders associated with the activity of cathepsin S, cannabinoid receptors type 1, tachykinin receptors type 1 and 2, prokineticin receptors type 1 and 2, bradykinin receptors type 1, melanocortin receptors MC4R, serotonin receptors 5-HT2B and NB-kB signaling pathway.

Furthermore, the invention relates to a pharmaceutical composition for preventing and/or treating obesity, psoriasis, Crohn's disease, colitis, irritable bowel syndrome, diarrhea, nausea and vomiting, and also other disorders associated with the activity of cathepsin S, cannabinoid receptors type 1, tachykinin receptors type 1 and 2, prokineticin receptors type 1 and 2, bradykinin receptors type 1, melanocortin receptors MC4R, serotonin receptors 5-HT2B and NB-kB signaling pathway, comprising an effective amount of Compound 1 according to the invention and at least one pharmaceutically acceptable excipient. In some embodiments of the invention, the excipient is a pharmaceutically acceptable carrier and/or excipient.

The invention also comprises a method for preventing and/or treating a disorder associated with the activity of cathepsin S, cannabinoid receptors type 1, tachykinin receptors type 1 and 2, prokineticin receptors type 1 and 2, bradykinin receptors type 1, melanocortin receptors MC4R, serotonin receptors 5-HT2B and NB-kB signaling pathway, in a body, comprising administering to said body a pharmaceutical composition according to the invention. In some non-limiting variants of the embodiment of the invention, the disease is obesity, psoriasis, Crohn's disease, colitis, irritable bowel syndrome, diarrhea, nausea and vomiting. In particular embodiments of the invention, the body is a human or animal body.

The invention relates to a method of preventing and/or treating a disorder associated with the activity of cathepsin S, cannabinoid receptors type 1, tachykinin receptors type 1 and 2, prokineticin receptors type 1 and 2, bradykinin receptors type 1, melanocortin receptors MC4R, serotonin receptors 5-HT2B and NB-kB signaling pathway, in a subject in need of such treatment, comprising administering a therapeutically effective amount of Compound 1 to said subject.

The invention also relates to a method of preventing and/or treating obesity, psoriasis, Crohn's disease, colitis, irritable bowel syndrome, diarrhea, nausea and vomiting obesity, psoriasis, Crohn's disease, colitis, irritable bowel syndrome, diarrhea, nausea and vomiting, in a subject in need of such treatment, including administering a therapeutically effective amount of Compound 1 to said subject.

The invention also relates to the use of Compound 1 in the manufacture of a medicament.

The present invention also relates to a combination comprising Compound 1 in combination with one or more other additional therapeutic agents.

DETAILED DISCLOSURE OF THE INVENTION

The obtainment of Compound 1 that is the object of the present invention is described in international application WO 2006101422. The indicated application discloses phenyl-containing N-acyl derivatives of biogenic amines and amino acids, which have the ability to inhibit cyclooxygenases. And, in turn, possessing analgesic and anti-inflammatory properties, without side effects, in particular ulcerogenic action and prospastic action, the ability to potentiate the action of other analgesics that have, in addition, antihypoxic, antidepressant and antiparkinsonian action.

During the large-scale screening of pharmacological targets of Compound 1 it has been surprisingly found that Compound 1 is a cathepsin S inhibitor, cannabinoid receptor type 1 agonist, tachykinin receptor type 1 and 2 antagonist, prokineticin receptor type 1 and 2 antagonist, bradykinin receptor type 1 antagonist, melanocortin receptor MC4R antagonist, 5-HT2B serotonin receptor antagonist and NB-kB signaling pathway inhibitor.

In accordance with the spectrum of the experimentally determined therapeutic targets of Compound 1, indications in which the use of Compound 1 seemed to be the most promising were determined. However, during the study of the pharmacokinetics of Compound 1, it was unexpectedly found that Compound 1 has extremely low stability in the blood plasma of animals and humans. This unexpected property of Compound 1 allows the compound to have the exclusively local effect. Thus, the use of Compound 1 will be safe, because there will be no systemic side effects associated with the multitarget action of the drug.

Thus, Compound 1 is a novel cathepsin S inhibitor, cannabinoid receptor type 1 agonist, tachykinin receptor type 1 and 2 antagonist, prokineticin receptor type 1 and 2 antagonist, bradykinin receptor type 1 antagonist, melanocortin receptor MC4R antagonist, 5-HT2B serotonin receptor antagonist and NB-kB signaling pathway inhibitor, that may be used for the treatment of obesity, psoriasis, Crohn's disease, colitis, irritable bowel syndrome, diarrhea, nausea and vomiting, and also other diseases associated with the activity of cathepsin S, cannabinoid receptors type 1, tachykinin receptors type 1 and 2, prokineticin receptors type 1 and 2, bradykinin receptors type 1, melanocortin receptors MC4R, serotonin receptors 5-HT2B and NB-kB signaling pathway. Pharmacokinetic parameters allowing to use the compound for topical use provide high safety and lack of systemic effects when using Compound 1.

Terms and Definitions

Term "Compound 1" relates to benzyl (2S)-2-[2-(4-hydroxyphenyl)acetamido]-3-phenylpropanoate compound that is also represented by the structural formula:

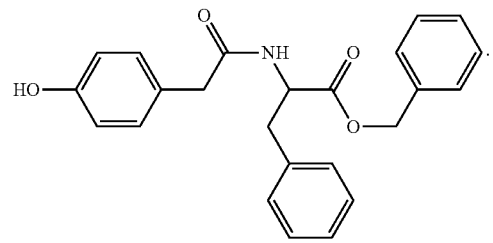 [SMILES: O=C(Cc1ccc(O)cc1)NC(Cc1ccccc1)C(=O)OCc1ccccc1]

Term "C" when it is used with a reference to temperature means the centigrade scale or the temperature scale of Celsius.

The term "$IC_{50}$" means a concentration of the compound under study at which a half maximal enzyme inhibition or agonistic or antagonistic action is achieved.

The term "pharmaceutically acceptable adducts" or "adducts" includes the product of the direct attachment of molecules to each other, which are obtained using relatively non-toxic compounds. Examples of pharmaceutically acceptable non-toxic adducts can be adducts formed by non-toxic nitro-derivatives or urea. Other pharmaceutically acceptable adducts include adducts of non-ionic surfactants, cyclodextrins and others, as well as charge transfer complexes (t-adducts). It should be noted that the term "adducts" also includes nonstoichiometric adducts.

The term "solvate" is used to describe a molecular complex containing a compound according to the invention and one or more molecules of a pharmaceutically acceptable solvent, for example ethanol. The term "hydrate" is used when the indicated solvent is water.

The term "excipient" means any pharmaceutically acceptable substance of inorganic or organic origin, which is part of the drug or is used in the production process, the manufacture of the drug to impart it the necessary physicochemical properties.

The term "AUC" (area under the curve) means a pharmacokinetic parameter characterizing the total concentration of a drug in the blood plasma during the entire observation time. It is mathematically defined as the integral from 0 to ∞ of the function of the drug concentration (pharmacokinetic curve) in the blood plasma from the time and is equal to the area of the figure limited by the pharmacokinetic curve and coordinate axes.

Terms "treatment", "therapy" encompass the treatment of pathological conditions in mammals, preferably in human, and include: a) reducing, b) blocking (suspending) of the disease course, b) alleviating the severity of the disease, i. e. inducing the regression of the disease, d) reversing the disease or condition, to which the term is applied, or one or more symptoms of the disease or condition.

The term "prophylaxis", "prevention" encompasses the elimination of risk factors, as well as the prophylactic treatment of sub-clinical stages of the disease in mammals, preferably, in human, directed to reducing the likelihood of origin of clinical stages of the disease. Patients for the prophylactic therapy are selected based on factors which, on the basis on known data, involve the increase in the risk of origin of clinical stages of the disease as compared with the total population. The prophylactic therapy includes a) primary prophylaxis and b) secondary prophylaxis. The primary prophylaxis is defined as the prophylactic treatment in patients who have not yet reached the clinical stage of the disease. The secondary prophylaxis is the prevention of the repeated onset of the same or close clinical state of the disease.

The use of Compound 1, which is the object of the invention, may be used for treating obesity, psoriasis, Crohn's disease, colitis, irritable bowel syndrome, diarrhea, nausea and vomiting, and also other diseases associated with the activity of cathepsin S, cannabinoid receptors type 1, tachykinin receptors type 1 and 2, prokineticin receptors type 1 and 2, bradykinin receptors type 1, melanocortin receptors MC4R, serotonin receptors 5-HT2B and NB-kB signaling pathway.

A Method of Therapeutical Use of Compounds

The subject matter of the invention also includes the administration to a subject in need of appropriate treatment of a therapeutically effective amount of Compound 1 according to the invention. A therapeutically effective amount means such an amount of a compound administered or delivered to a patient at which the patient is most likely to display the desired response to the treatment (prophylaxis). The precise required amount may vary from subject to subject depending on the age, body weight and general patient's condition, the severity of disease, the procedure of administration of the preparation, the combined treatment with other preparations and the like.

The compound according to the invention or a pharmaceutical composition comprising the compound can be administered to the patient's body in any amount and by any way of administration that is effective for the treatment or prophylaxis of the a disease. Preferably, the daily dose of the active substance is 5 g for a patient per day, the most preferably the daily dose is 5-500 mg/day. Preferably, Compound 1 is administered orally or topically.

After mixing Compound 1 with a suitable pharmaceutically acceptable carrier in the desired dosage, pharmaceutical compositions that are the essence of the invention can be administered to the body of humans or other animals orally, parenterally, topically, and the like.

The administration may take place both once and several times a day, a week (or at any other time interval), or time from time. Besides, Compound 1 can be administered to the patient's body daily for a certain period of time, for example 2-10 days, followed by a period without the intake of the substance, for example, 1-30 days.

When Compound 1 is used as the part of combination therapy regimen, the dose of each of components of the combination therapy is administered during the required treatment period. The compounds constituting the combination therapy can be administered to the patient's body both at a time, in the dosage form containing all the components, and in the form of individual dosages of the components.

Pharmaceutical Compositions (Drugs)

The invention also relates to a pharmaceutical composition that comprises Compound 1 according to the invention or an adduct, hydrate, solvate thereof, and one or more pharmaceutically acceptable carriers, adjuvants, solvents and/or excipients, such as may be administered to the patient in combination with the compound that is the essence of the present invention, and which do not affect the pharmacological activity of the compound and are non-toxic when administered in doses sufficient to deliver a therapeutic amount of the compound. The pharmaceutical compositions claimed herein comprise Compound 1 of the present invention together with pharmaceutically acceptable carriers, which may include any solvents, diluents, dispersions or suspensions, surfactants, isotonic agents, thickeners and emulsifiers, preservatives, binders, glidants etc. suitable for the particular dosage form.

Materials that can serve as pharmaceutically acceptable carriers include, but are not limited to, mono- and oligosaccharides, as well as their derivatives; gelatin; talc; excipients such as cocoa butter and suppository waxes; oils such as peanut, cottonseed, saffrole, sesame, olive, corn and soybean oil; glycols such as propylene glycol; esters such as ethyl oleate and ethyl laurate; agar; buffering agents such as magnesium hydroxide and aluminum hydroxide; alginic acid; pyrogen-free water; isotonic solution, Ringer's solution; ethyl alcohol and phosphate buffer solutions.

The composition may also comprise other nontoxic compatible lubricants such as sodium lauryl sulfate and magnesium stearate, and also dyes, film formers, sweeteners, flavoring and perfuming agents, preservatives and antioxidants.

The object of the invention are also dosage forms—a class of pharmaceutical compositions, the formulation of which is optimized for a particular way of the administration to the body in a therapeutically effective dose, e.g., for oral, topical administration, or the administration by inhalation, e.g., in the form of the inhalation spray, or by intravascular method, intranasally, subcutaneously, intramuscularly, as well as by infusion method, in the recommended dosages.

Dosage forms of the invention may comprise formulations obtained by methods of the use of liposomes, microencapsulation techniques, methods of the preparation of nanoforms of the medicament or other methods known in the pharmaceutics.

Pharmaceutical compositions of the present invention may be obtained by mixing Compound 1 with a pharmaceutically acceptable carrier.

Thus, in the obtainment of the composition, e.g. in the form of a tablet, Compound 1 is mixed with one or more pharmaceutical excipients, such as gelatin, starch, lactose, magnesium stearate, talc, silica, arable gum, mannitol, microcrystalline cellulose, hypromellose, or analogous compounds.

Tablets may be coated with sucrose, cellulose derivative or other substances suitable for applying a coating. The tablets may be obtained by different methods such as direct compression, dry or wet granulation, or hot melt fusion.

A pharmaceutical composition in the form of a gelatin capsule may be obtained by mixing Compound 1c with a pharmaceutically acceptable carrier (it is not clear what other substances), and filling soft or solid capsules with the obtained mixture.

For the parenteral administration, aqueous suspensions, isotonic saline solutions or sterile solutions for injections are used, which contain pharmacologically compatible agents, for example propylene glycol or butylene glycol, are used.

Examples of Pharmaceutical Compositions

A substance described in the invention may be used for the prevention and/por treatment of human diseases or animals diseases in the form of the following formulations: (the active ingredient—Compound 1—is meant under the "Substance"):

Tablet I mg/tablet
Substance 3.0
Microcrystalline cellulose 64.0
Sodium carboxymethyl starch 2.3
Magnesium stearate 0.7
Tablet II mg/tablet
Substance 30.0
Microcrystalline cellulose 640.0

Sodium carboxymethyl starch 23.0
Magnesium stearate 7.0
Tablet III mg/tablet
Substance 3.0
Microcrystalline cellulose 64.0
Sodium carboxymethyl starch 2.3
Magnesium stearate 0.7
Enteric coating Acryl-EZE® MP 2.0
Tablet IV mg/tablet
Substance 30.0
Microcrystalline cellulose 640.0
Sodium carboxymethyl starch 23.0
Magnesium stearate 7.0
Enteric coating Acryl-EZE® MP 20.0
Tablet V mg/tablet
Substance 200.0
Lactose Ph. Eur 182.75
Sodium croscarmellose 12.0
Corn starch (5% w/v paste) 2.25
Magnesium stearate 3.0
Capsule mg/capsule
Substance 10.0
Lactose Ph. Eur 488.5
Magnesia 1.5
Formulation for injections I mg/100 ml
Substance 310.0
Polyethylene glycol-400 44.4
Disodium edetate 5.0
Water for injections up to 100 ml
Ointment I g/100 g
Substance 0.103
Tocopherol 0.100
Lanett SX 10.900
Castor oil 11.000
Polyethylene oxide 1500 31.906
Polysorbate 80 4.491
1,2-Propanediol 41.500
Ointment II g/100 g
Substance 0.103
Butylhydroxytoluene (ionol) 0.100
Lanett SX 10.900
Castor oil 11.000
Polyethylene oxide 1500 31.906
Polysorbate 80 4.491
1.2-Propanediol 41.500
Ointment III g/100 g
Substance 0.105
Tocopherol 0.100
Lanett SX 10.900
Castor oil 11.000
Polyethylene oxide 1500 31.906
Polysorbate 80 2.225
1.2-Propanediol 41.500
Ethyl alcohol, rectified 2.260
Ointment IV g/100 g
Substance 0.105
Butylhydroxytoluene (ionol) 0.100
Lanett SX 10.900
Castor oil 11.000
Polyethylene oxide 1500 31.906
Polysorbate 80 4.491
1.2-Propanediol 41.500
Ethyl alcohol, rectified 2.260
These compositions can be prepared in accordance with standard pharmaceutical techniques.

Use of Compound 1 in Combination Therapy

Despite the fact that Compound I according to the invention may be administered as an individual active pharmaceutical agent, it may also be used in combination with one or more other agents, in particular, the other agent may be an antibiotic, NSAID or other anti-inflammatory agent, an antibody, an analgesic, cytostatic, etc. In case of the combination intake, therapeutic agents may represent different dosage forms that are administered simultaneously or sequentially at different times, or the therapeutic agents may be combined in one dosage form.

The phrase "combination therapy" with respect to Compound 1 of the invention in combination with other pharmaceutical agents is sequential or simultaneous intake of all agents that somehow provides the beneficial effect of the combination of drugs. The combined administration means, in particular, the combined delivery, e.g. in one tablet, capsule, injection or in the other form having a fixed ratio of active substances, as well as the simultaneous delivery in several separate dosage forms for each compound respectively.

Thus, the administration of compounds of the invention may be carried together with additional therapies known to those skilled in the field of the prevention and treatment of corresponding diseases, including the use of antibacterial, cytostatic and cytotoxic drugs, medicaments for inhibiting symptoms or side effects of one of medicaments.

If the dosage form is a single dosage form, the combination uses the compounds of the invention in a suitable dosage range. Compound 1 according to the invention may also be administered to the patient sequentially with other agents, in the case where the combination of these medicaments is not possible. The invention is not limited to the sequence of administration; the compound of the invention may be administered to the patient together, before or after the administration of another medicament.

EXAMPLES

The Obtainment of the Compound According to the Invention

The obtainment of Compound 1 is described and disclosed in international application WO 2006101422. The ability of Compound 1 to inhibit the activity of cyclooxygenases is described and disclosed in the same application.

The Characteristic of the Biological Activity of the Compound According to the Invention The biological activity of Compound 1 that is the object of the invention has been studied in different in vitro and in vivo experiments. In particular, upon the study of the activity of Compound 1 in different in vitro and in vivo models, the inhibitory effect of Compound 1 in a mouse model of diarrhea induced by castor oil has been shown. The biological effect of Compound 1 cannot be predicted or explained on the basis of prior knowledge about the ability of Compound 1 to inhibit cyclooxygenases.

Studies of the biological activity of Compound 1 in vitro have allowed to establish that Compound 1 is a cathepsin S enzyme inhibitor, cannabinoid receptor type 1 agonist, tachykinin receptor type 1 and 2 antagonist, prokineticin receptor type 1 and 2 antagonist, bradykinin receptor type 1 antagonist, melanocortin receptor MC4R antagonist and NB-kB signaling pathway inhibitor. Probably, the activity of Compound 1 in psoriasis models, and also in different models of gastrointestinal disorders is provided by the influence on the aforesaid proteins.

Example 1. The Study of the Effect of Compound 1 on the Enzymatic Activity of Cathepsin S Compound 1 was dissolved in DMSO to a concentration of 100 mM; then a stock solution was serially diluted with DMSO. The maximum starting concentration of the substance is 100 µM. The effect was determined at 5 concentrations of the tested compounds, each concentration was studied twice. A human recombinant cathepsin S, expressed in E. coli was used in the experiment. Test compounds were preincubated for 15 minutes at 37° C. with an enzyme whose activity was determined by the rate of transformation of the substrate Z-Phe-Arg-AMC (6 µM) by the fluorescence spectroscopy (Protein Sci. 1996 April; 5(4):789-91).

As the result of the study, it has been established that Compound 1 is the cathepsin S inhibitor with $IC_{50}$=6.7 µM.

Example 2. The Study of the Effect of Compound 1 on the Activity of the Tachykinin Receptor Type 1 (NK1R)

Compound 1 dissolved in DMSO to a concentration of 100 mM; then a stock solution was serially diluted with DMSO. The maximum starting concentration of the substance is 100 µM. The effect was determined at 5 concentrations of the tested compounds, each concentration was studied twice. U373 cells expressing NK1R were used in the experiment, said cells, after the preincubation with an [Sar9, Met(O2)11]-SP (1 nM) antagonist, were incubated with Compound 1. The activity of receptors was determined according to the intracellular calcium concentration by the fluorescence spectroscopy (Glia. 1992; 6(2):89-95).

As the result of the study, it has been established that Compound 1 is the tachykinin receptor type 1 antagonist with $IC_{50}$=4.1 µM.

Example 3. The Study of the Effect of Compound 1 on the Activity of the Tachykinin Receptor Type 2 (NK2R)

Compound 1 was dissolved in DMSO to a concentration of 100 mM; then a stock solution was serially diluted with DMSO. The maximum starting concentration of the substance is 100 µM. The effect was determined at 5 concentrations of the tested compounds, each concentration was studied twice. CHO cells expressing NK2R were used in the experiment, said sells, after the preincubation with an [Nleu10]-NKA-(4-10) (10 nM) agonist, were incubated with the test compound. The activity of receptors was determined according to the intracellular calcium concentration by fluorescence spectroscopy (Biochem Biophys Res Commun. 1994 May 16; 200(3):1512-20).

As the result of the study, it has been established that Compound 1 is the tachykinin receptor type 2 antagonist with $IC_{50}$=8.4 µM.

Example 4. The Study of the Effect of Compound 1 on the Activity of the Cannabinoid Receptor Type 1

Compound 1 was dissolved in DMSO to a concentration of 100 mM; then the stock solution was serially diluted with DMSO. The maximum starting concentration of the substance is 100 µM. The effect was determined at 5 concentrations of the tested compounds, each concentration was studied twice. CHO cells expressing CB1R were used in the experiment, these cells were incubated with the test compound. CP55940 (30 nM) compound was used as the control. The activity of receptors was determined by the intracellular calcium concentration by the homogeneous time resolved fluorescence spectroscopy (Mol Pharmacol. 1995 September; 48(3):443-50).

As the result of the study, it has been established that Compound 1 is the cannabinoid receptor type 1 agonist with $IC_{50}$=3.3 µM.

Example 5. The Study of the Effect of Compound 1 on the Activity of Bradykinin Receptor BRDKB1

Compound 1 was dissolved in DMSO to a concentration of 100 mM; then a stock solution was serially diluted with DMSO. The maximum starting concentration of the substance is 100 µM. The effect was determined at 5 concentrations of the tested compounds, each concentration was studied twice. CHO cells expressing bradykinin receptors B1 were used in the experiment, these cells, after preincubation with a LysdesArg9-BK agonist (3 nM), were incubated with the test compound. The activity of receptors was determined according to the intracellular calcium concentration by fluorescence spectroscopy (Eur J Pharmacol. 2000 Mar. 24; 392(1-2):1-9).

As the result of the study, it has been established that Compound 1 is the bradykinin receptor antagonist with $IC_{50}$=3.7 µM.

Example 6. The Study of the Effect of Compound 1 on the Activity of Prokineticin Receptors Type 1 (PK1)

Compound 1 was dissolved in DMSO to a concentration of 100 mM; then a stock solution was serially diluted with DMSO. The maximum starting concentration of the substance is 100 µM. The effect was determined at 5 concentrations of the tested compounds, each concentration was studied twice. HEK-293 cells expressing prokineticin receptors PK1 were used in the experiment, these cells, after preincubation with a PK1 agonist (3 nM), were incubated with the test compound. The activity of receptors was determined according to the intracellular calcium concentration by the fluorescence spectroscopy (Mol Pharmacol. 2005 June; 67(6):2070-6).

As the result of the study, it has been established that Compound 1 is the prokineticin receptor type 1 (PK1) antagonist with $IC_{50}$=5.7 µM.

Example 7. The Study of the Effect of Compound 1 on the Activity of Prokineticin Receptors Type 2 (PK2)

Compound 1 was dissolved in DMSO to a concentration of 100 mM; then a stock solution was serially diluted with DMSO. The maximum starting concentration of the substance is 100 µM. The effect was determined at 5 concentrations of the tested compounds, each concentration was studied twice. HEK-293 cells expressing prokinetycin receptors PK2 were used in the experiment, these cells, after preincubation with a PK2 agonist (2 nM), were incubated with the test compound. The activity of receptors was determined according to the intracellular calcium concentration by the fluorescence spectroscopy (Mol Pharmacol. 2005 June; 67(6):2070-6).

As the result of the study, it has been established that Compound 1 is the prokineticin receptor type 2 (PK2) antagonist with $IC_{50}$=5.4 µM.

Example 8. The Study of the Effect of Compound 1 on the Activity of Melanocortin Receptors MC4R Compound 1 was dissolved in DMSO to a concentration of 100 mM; then a stock solution was serially diluted with DMSO. The maximum starting concentration of the substance is 100 µM. The effect was determined at 5 concentrations of the tested compounds, each concentration was studied twice. CHO cells expressing a melanocortin receptor MC4R were used in the experiment, these cells, after preincubation with a NDP-alpha-MSH agonist (30 nM), were incubated with the test compound. The activity of receptors was determined according to the intracellular calcium concentration by the homogeneous time resolved fluorescence spectroscopy.

As the result of the study, it has been established that Compound 1 is the melanocortin receptor MC4R antagonist with $IC_{50}$=7.6 µM.

Example 9. The Study of the Effect of Compound 1 on the Activity of Serotonin Receptors 5-HT2B Compound 1 was dissolved in DMSO to a concentration of 100 mM; then a stock solution was serially diluted with DMSO. The maximum starting concentration of the substance is 100 µM. The effect was determined at 5 concentrations of the tested compounds, each concentration was studied twice. CHO cells expressing serotonin receptors 5-HT2B were used in the experiment, these cells, after preincubation with a serotonin agonist (30 nM), were incubated with the test compound. The activity of receptors was determined according to the intracellular calcium concentration of phosphatidylinositol by the homogeneous time resolved fluorescence spectroscopy (Br J Pharmacol. 1999 September; 128(1):13-20).

As the result of the study, it has been established that Compound 1 is the serotonin receptor 5-HT2B antagonist with $IC_{50}$=8.9 µM.

Example 10. The Study of the Effect of Compound 1 on the Activity of NF-kB Signaling Pathway Compound 1 was dissolved in DMSO to a concentration of 100 mM; then a stock solution was serially diluted with DMSO. The maximum starting concentration of the substance is 100 µM. The effect was determined at 5 concentrations of the tested compounds, each concentration was studied twice. Human Jurkat T lymphocytes transfected with the lacZ operon in which β-galactosidase transcription was under the control of the NFAT-1 transcription factor were used in the experiment. The test compound were preincubated with cells. The β-galactosidase activity of the cells was determined by the rate of transformation of the substrate FDG (fluorescein-di-β-D-galactopyranoside) by the fluorescence spectrophotometry.

As the result of the study, it has been established that Compound 1 is the NF-kB signaling pathway inhibitor with $IC_{50}$=9.9 µM.

Example 11. The Study of the Effect of Compound 1 on a Mouse Model of Imiquimod-Induced Ear Psoriasis Psoriasis was simulated in female balb/c mice by applying Aldar cream (5% imiquimod) on the inner side of the right ear daily 1 time per day for 10 days (J Immunol. 2009 May 1; 182(9):5836-45). Vaseline was applied to intact animals: 20 mg on the right ear.

The assessment of the development of pathology was performed on $2^{nd}$, $4^{th}$, $6^{th}$, $8^{th}$ and $10^{th}$ day before the next application of Aldar cream by measuring the thickness of the left and right ears.

The results of the study are presented in table 1.

TABLE 1

The gain in the thickness of the right (affected) ear on the specific day of the study relatively the thickness of the right (affected) ear on day 0 of the study when studying the activity of Compound 1 on a mouse model of ear psoriasis, % (M ± m, n = 10)

| Group | Days of the study | | | | |
|---|---|---|---|---|---|
| | 2 | 4 | 6 | 8 | 10 |
| Intact | 18.5 ± 4.6 | 20.6 ± 5.6 | 27.8 ± 5.4 | 32.6 ± 6.1 | 44.8 ± 8.3 |
| Control without placebo | 106.5 ± 9.4* | 109.2 ± 12.9* | 130.4 ± 16.1* | 133.1 ± 19.5* | 113.5 ± 16.0* |
| Control treated with placebo | 40.9 ± 2.6 | 45.2 ± 1.0*& | 60.0 ± 2.0*& | 67.8 ± 6.0*& | 69.4 ± 8.7& |
| Compound 1 (0.3% ointment) | 14.1 ± 3.2& | 22.1 ± 5.3&$ | 28.0 ± 7&$ | 19.4 ± 4.7&$ | 7.9 ± 3.1*&$ |
| Dermovate (clobetasol) 0.05% | 18.9 ± 5.6& | 22.6 ± 5.3&$ | 24.6 ± 7.5&$ | 21.3 ± 4.9&$ | 16.5 ± 3.0*&$ |

Notes:
*distinctions are statistically significant as compared to intact (p < 0.05);
$is statistically significant as compared to the corresponding group "Control treated with placebo), at p < 0.05;
&is statistically significant as compared to the corresponding group "Control without placebo), at p < 0.05.

It is obvious from table 1 that Compound 1 has reduced the gain in the thickness of the right (affected) ear of mice to the level of intact animals.

Thus, Compound 1 has the pronounced effect in the mouse model of ear psoriasis, as well as the glucocorticosteroid drug Dermovate (clobetasol) intended for the treatment of psoriasis.

Example 12. The Study of the Effect of Compound 1 on a Mouse Model of Imiquimod-Induced Psoriasis on the Back Psoriasis was simulated in female balb/c mice by applying Aldar cream (5% imiquimod) on a previously shaved skin back area of 3×4 cm daily 1 time per day for 15 days (J Immunol. 2009 May 1; 182(9):5836-45). Intact animals were applied with vaseline: 120 mg per the shaved back area.

The assessment of the development of pathology was performed on the $10^{th}$, $12^{th}$, $13^{th}$ and $15^{th}$ day before the next application of Aldar cream according to the index: the thickness of the skin fold on the back. The thickness of the skin fold on the back was measured with a Digimatic MK-25 micrometer (Mitutoyo, Japan).

The results of the study are presented in table 2.

TABLE 2

The gain of the thickness of the back skin at a certain day of the study to the thickness of the skin back before the start of the study of the activity of Compound 1 on the model of psoriasis on the back, % (M ± m, n = 10)

| Group | Days of the study | | | |
|---|---|---|---|---|
| | 10 | 12 | 13 | 15 |
| Intact | 6.8 ± 3.5 | 7.8 ± 3.9 | 8.7 ± 4 | 9.8 ± 4 |
| Control treated with placebo | 36.2 ± 3.8* | 41.6 ± 4.9* | 40.9 ± 4.8* | 41.4 ± 5* |
| Compound 1 (0.3% ointment) | 23.1 ± 4.6*& | 19.9 ± 4.4& | 20.5 ± 4.5& | 22.4 ± 4.5& |
| Dermovate (clobetasol) 0.05% | −26.8 ± 7.6*& | death of the whole group | death of the whole group | death of the whole group |

It is clear from table 2 that Compound 1 has reduced the gain of the thickness of the skin fold of the affected skin area by 2 times. The comparison drug—Dermovate—has shown the toxic effect by thinning the skin and causing the total death of animals on the $12^{th}$ day of the study.

Thus, it is possible to conclude that on the mouse model of psoriasis on the back Compound 1 has the pronounced therapeutic effect, reducing the gain of skin thickness of the affected area. Compared to the safety profile, Compound 1 surpasses Dermovate.

Example 13. The Study of the Effect of Compound 1 on a Mouse Model of Crohn's Disease The study was performed on male balb/c mice. Animals, which starved for 24 hours, were injected with 150 µl/mouse of TNBS solution in 50% ethanol into the rectal hole of the mouse to the depth of 4 cm using a 3.5 F catheter. Next, the mice were turned upside down and held for 60 seconds. 150 µl of the 50% ethanol solution was injected into the healthy control (intact animals). The study lasted 7 days. The development of pathology was assessed by the death of animals.

TABLE 4

Death of animals during the study of the activity of Compound 1 on the model of Crohn's disease

| Groups | Regimen of administration of XC173 or prednisolone | A dose of TNBS, mg/kg | The initial quantity of animals in the group | The portion of dead animals, % |
|---|---|---|---|---|
| Intact | — | — | 10 | 0 |
| Control | — | 4.5 | 10 | 80 |
| Compound 1 (50 mg/kg) | 1 time per day | | 10 | 30 |
| Prednisolone (5 mg/kg) | 1 time per day | | 10 | 80 |
| Prednisolone (10 mg/kg) | | | 10 | 60 |

From the data shown in Table 4, it can be seen that the administration of Compound 1 has allowed to decrease the death of animals by more than 2 times. In terms of severity of the action, Compound 1 is superior to the steroid drug prednisone, which has reduced the mortality by 20-40%.

Example 14. The Study of the Activity of Compound 1 on a Mouse Model of Indomethacin Colitis The study was performed on male Wistar rats, which were subcutaneously injected with an indomethacin solution in a dose of 9 mg/kg for two days running to induce colitis. The injection solution was prepared as follows: first, indomethacin was dissolved in 100% ethanol, then it was diluted in 5% $NaHCO_3$ solution. On the $4^{th}$ day after euthanasia, the stomach and intestine were removed from the animals in the CO2 chamber, then the caecum was excised, 10 cm from the ileum and large intestine was cut off, and 5 cm—from the caecum, to assess gross lesions (J Ethnopharmacol. 2004 February; 90(2-3): 195-204).

TABLE 5

The macroscopic assessment of the lesion of the caecum, ileum and large intestine while testing Compound 1 on a model of colitis induced by the administration of indomethacin, points (M ± m, n = 10)

| Group | Macroscopic assessment of the lesion, points (only animals with the pathology were considered) | | | |
|---|---|---|---|---|
| | Ileum | Large intestine | Caecum | Overall assessment |
| Intact | 0.0 ± 0.0 | 0.0 ± 0.0 | 0.0 ± 0.0 | 0.0 ± 0.0 |
| Indomethacin (9 mg/kg) | 5.6 ± 1.2* | 1.2 ± 0.3* | 1.2 ± 0.4* | 8.0 ± 1.3* |
| Compound 1 (100 mg/kg) | 0.6 ± 0.3& | 0.2 ± 0.1& | 0.4 ± 0.2 | 1.2 ± 0.4*& |
| Prednisolone (2 mg/kg) | 0.6 ± 0.6& | 0.4 ± 0.2 | 0.3 ± 0.2& | 1.3 ± 0.9& |

Note:
*distinctions are statistically significant as compared to the intact group ($p < 0.05$);
&distinctions are statistically significant as compared to the control group ($p < 0.05$).

It is clear from Table 6 that Compound 1 has reduced the degree of intestinal lesion. Thus, it can be concluded that Compound 1 has the pronounced therapeutic effect on the mouse model of indomethacin colitis.

Example 15. The Study of the Activity of Compound 1 on a Mouse Model of Diarrhea Induced by Castor Oil Balb/c mice, which starved for 24 hours, were given castor oil intragastrically. Then the animals were encaged into individual cages with a bottom covered with white paper, and time before the onset of diarrhea was noted. The observation time is 4 hours (J Pharm Pharmacol. 2015 February; 67(2):244-54).

TABLE 6

The time of onset of diarrhea when studying the activity of Compound 1 on the model of diarrhea caused by castor oil, min (M ± m, n = 10)

| Groups | A quantity of animals in the group | The time of onset of diarrhea, min |
|---|---|---|
| Intact | 10 | No diarrhea occurred within 4 hours |
| Control | 10 | 23.00 ± 2.51 |
| Compound 1 (50 mg/kg) | 10 | 42.00 ± 3.43& |
| Loperamide (1 mg/kg) | 10 | 56.40 ± 5.14& |

TABLE 6-continued

The time of onset of diarrhea when studying the activity of Compound 1 on the model of diarrhea caused by castor oil, min (M ± m, n = 10)

| Groups | A quantity of animals in the group | The time of onset of diarrhea, min |
|---|---|---|
| Drotaverine (1 mg/kg) | 10 | 43.60 ± 2.61& |

Notes:
&distinctions are statistically significant as compared to the control group ($p < 0.05$).

It can be seen from Table 6 that the administration of Compound 1 has increased the time to the onset of diarrhea by 2 times. This provides grounds to conclude that Compound 1 has the pronounced therapeutic effect in models of gastrointestinal disorders.

Example 16. The Study of the Effect of Compound 1 on a Model of Irritable Bowel Syndrome The effect on the motility of the gastrointestinal tract was studied on a model of irritable bowel syndrome in nonlinear male mice weighing 24-30 g. The animals were intragastrically injected with a solution of activated carbon (50 mg/ml, in a volume of 10 ml/kg) and the speed (in minutes) of the movement of activated coal through the intestines of animals. The compounds under study were intragastrically administered once 1 hour before the introduction of activated carbon. Drotaverine (6.7 mg/kg), Buscopan (3 mg/kg) and Trimedat (33 mg/kg) were used as reference drugs.

TABLE 7

Results of the study of the effect of Compound 1 on the motility of the gastrointestinal tract in vivo

| Groups | The way of administration | N | The evacuation speed of activated carbon, min |
|---|---|---|---|
| Intact | Once intragastrically 1 hour before the administration of activated carbon | 30 | 66.47 ± 3.44 |
| Compound 1 (0.5 mg/kg) | | 20 | 89.45 ± 1.9* |
| Compound 1 (1.5 mg/kg) | | 20 | 104.25 ± 5.49* |
| Compound 1 (5 mg/kg) | | 30 | 107.67 ± 3.07* |
| Compound 1 (10 mg/kg) | | 10 | 126.6 ± 3.66* |
| Compound 1 (15 mg/kg) | | 30 | 123.13 ± 5.27* |
| Compound 1 (50 mg/kg) | | 30 | 129.13 ± 3.19* |
| Compound 1 (150 mg/kg) | | 30 | 135.63 ± 2.87* |
| Drotaverine (6.7 mg/kg) | | 20 | 105.85 ± 2.39* |
| Buscopan (3 mg/kg) | | 20 | 73.2 ± 2.87 |
| Trimedat (33 mg/kg) | | 20 | 83.65 ± 2.42* |

It is clear from table 7 that the administration of Compound 1 has increased the evacuation time of activated carbon by 2 times. This provides grounds to conclude that Compound 1 has the pronounced spasmolityc effect.

Example 17. The Study of the Stability of Compound in Blood Plasma of Animals and Human Compound 1 at a concentration of 1 µM was incubated for 24 hours in the blood plasma of human and various animal species (rats, mice, guinea pigs, rabbits, horses, dogs, bull, pygmy hogs) at 37° C. Aliquots were taken at time points of 0, 0.25, 1, 2, 4, 8 and 24 hours. In the case of blood plasma of rabbits and monkeys, Compound 1 was incubated for 4 hours, and aliquots were taken at time points 0, 0.25, 1, 4. After the protein precipitation with acetonitrile, samples were analyzed by HPLC-MS/MS to determine the concentration of Compound 1. Verapamil was used as a stable control.

The carried studies have shown that Compound 1 already after 15 minutes is almost completely hydrolyzed in the blood plasma of mice, rats, rabbits and guinea pigs. For other types of animals, the stability of Compound 1 is increased among monkey-pygmy hog-man-dog. The results of the study are presented in table 8.

TABLE 8

The stability of Compound 1 in blood plasma of human and various animal species

| | | Content, % from the initial | |
|---|---|---|---|
| Animal specimen | Time, hour | Mean (n = 2) | SD |
| Human | 0 | 100 | 0.0 |
| | 0.25 | 85.4 | 5.1 |
| | 1 | 70.3 | 0.6 |
| | 2 | 50.1 | 4.3 |
| | 4 | 32.1 | 3.0 |
| | 8 | 16.4 | 2.4 |
| | 24 | 0.00 | 2.5 |
| Dog | 0 | 100 | 0.0 |
| | 0.25 | 110 | 18 |
| | 1 | 79.1 | 7.2 |
| | 2 | 80.6 | 25 |
| | 4 | 67.2 | 0.3 |
| | 8 | 54.1 | 2.5 |
| | 24 | 33.8 | 5.5 |
| Guinea pig | 0 | 100 | 0.0 |
| | 0.25 | 0.00 | 0.0 |
| | 1 | 0.00 | 0.0 |
| | 2 | 0.00 | 0.0 |
| | 4 | 0.00 | 0.0 |
| | 8 | 0.00 | 0.0 |
| | 24 | 0.00 | 0.0 |
| Monkey | 0 | 100 | 0.0 |
| | 0.25 | 38.3 | 3.2 |
| | 1 | 1.69 | 0.0 |
| | 4 | 0.00 | 0.0 |
| Mouse | 0 | 100 | 0.0 |
| | 0.25 | 0.00 | 0.0 |
| | 1 | 0.00 | 0.0 |
| | 2 | 0.00 | 0.0 |
| | 4 | 0.00 | 0.0 |
| | 8 | 0.00 | 0.0 |
| | 24 | 0.00 | 0.0 |
| Rat | 0 | 100 | 0.0 |
| | 0.25 | 0.00 | 0.0 |
| | 1 | 0.00 | 0.0 |
| | 2 | 0.00 | 0.0 |
| | 4 | 0.00 | 0.0 |
| | 8 | 0.00 | 0.0 |
| | 24 | 0.00 | 0.0 |
| Pygmy hog | 0 | 100 | 0.0 |
| | 0.25 | 92.6 | 0.4 |
| | 1 | 61.8 | 0.7 |
| | 2 | 35.9 | 1.0 |
| | | 15.9 | 2.5 |
| | 4 | 2.68 | 0.5 |
| | | 0.15 | 0.0 |
| Rabbit | 0 | 100 | 0.0 |
| | 0.25 | 0.00 | 0.0 |
| | 1 | 0.00 | 0.0 |
| | 4 | 0.00 | 0.0 |

Thus, during the study, the low stability of Compound 1 in the blood plasma of humans and various animal species was shown. This unexpected property of Compound 1 allows the compound to have the exclusively topical effect. Thus, the use of Compound 1 will be safe, because there will be no systemic side effects associated with the multitarget effect of the drug.

Example 18. The Study of Pharmacokinetics of Compound 1 in Blood Plasma of Animals after the Oral Administration To confirm low systemic availability of Compound 1, the study pharmacokinetics and bioavailability of Compound 1 after oral administration to rats in a dose of 3 mg/kg was conducted. Sampling of blood from animals was performed at specified time points for 24 hours after the drug administration. The content of Compound 1 in plasma samples was analyzed by HPLC-MS/MS, the limit of quantitation was 1 ng/ml.

In the course of the conducted exploration, Compound 1 was not detected in the blood plasma of experimental animals.

Example 19. The Study of the Influence of Chronic Oral Administration of Compound 1 Per a Body Weight of Rabbits The effect of 90-day, oral administration of Compound 1 in doses of 1.5 mg/kg, 7.5 mg/kg and 15 mg/kg on the body weight of male and female Chinchilla rabbits was studied. The general condition of the rabbits, appearance, and mobility throughout the whole experiment were satisfactory and did not differ in the experimental and control groups.

Animals treated with Compound 1 were somewhat lagging behind in weight gain compared with parallel controls. In male rabbits treated with Compound 1 in a dose of 1.5 mg/kg, the lag in body weight gain was noted on 4-5 and 9-11 weeks of the administration; in males who received the drug in a dose of 7.5 mg/kg—on 4-5 and 10-11 weeks; in males who received the drug in a dose of 15 mg/kg on 2; 4-5; 8-11 weeks of the experiment. In female rabbits, on the background of the daily intragastric administration of Compound 1 in a dose of 1.5 mg/kg, the lag in body weight gain was observed on weeks 5-6 and 9; on the background of doses of 7.5 mg/kg and 15 mg/kg—practically, during the entire period of the drug administration. In the recovery period, there were no differences in the dynamics of the body weight between the control and experimental animals. The decrease in the body weight gain in the experimental animals was accompanied by the decrease in feed and water intake.

These studies show that Compound 1 can also be effective in controlling body weight, and in case of obesity.

Thus, in the course of the conduced studies, it has been shown that Compound 1 is the cathepsin S inhibitor, cannabinoid receptor type 1 agonist, tachykinin receptor type 1 and 2 antagonist, prokineticin receptor type 1 and 2 antagonist, bradykinin receptor type 1 antagonist, melanocortin receptor MC4R antagonist, serotonin receptor 5-HT2B antagonist and NB-kB signaling pathway inhibitor. The effect on these therapeutic targets allows Compound 1 to have the pronounced therapeutic effect in models of obesity, psoriasis, Crohn's disease, colitis, irritable bowel syndrome and diarrhea. The extremely low stability of Compound 1 in the blood plasma of animals and humans allows to eliminate a possibility of side effects that could arise from the systemic use of such a multitarget agent.

Although the invention has been described with reference to the disclosed embodiments, it should be obvious to those skilled in the art that the specific experiments described in detail are given only to illustrate the present invention and should not be considered as limiting the scope of the invention in any way. It should be clear that it is possible to implement various modifications without the departure from the essence of the present invention.

The invention claimed is:

1. A method of preventing and/or treating a disorder selected from the group consisting of obesity, psoriasis, Crohn's disease, colitis, irritable bowel syndrome, diarrhea, nausea and vomiting in a subject in need of the treatment, comprising administering a therapeutically effective amount of a compound of the formula

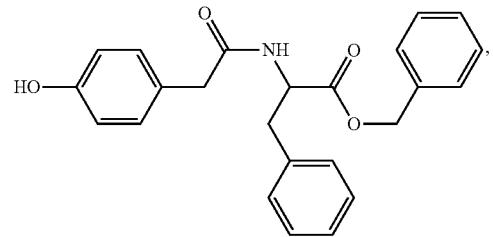 [SMILES: O=C(Cc1ccc(O)cc1)NC(Cc1ccccc1)C(=O)OCc1ccccc1]

or a hydrate or solvate thereof, to said subject.

2. The method of claim 1, wherein the disorder is associated with the activity of cathepsin S, and/or cannabinoid receptors type 1, and/or tachykinin receptors type 1 and 2, and/or prokineticin receptors type 1 and 2, and/or bradykinin receptors type 1, and/or melanocortin receptors MC4R, and/or serotonin receptors 5-HT2B and/or NB-kB signaling pathway.

* * * * *